United States Patent [19]

Liardet

[11] Patent Number: 5,451,190
[45] Date of Patent: Sep. 19, 1995

[54] APPARATUS FOR RESPIRATORY THERAPY

[75] Inventor: Claude Liardet, Aubonne, Switzerland

[73] Assignee: Varioraw Percutive S.A., Switzerland

[21] Appl. No.: 45,974

[22] Filed: Apr. 9, 1993

[30] Foreign Application Priority Data

Apr. 10, 1992 [CH] Switzerland ............... 1186/92

[51] Int. Cl.⁶ .................................................. A63B 23/18
[52] U.S. Cl. ........................................ 482/13; 128/200.24
[58] Field of Search .................. 482/13; 128/200.14, 128/200.23, 200.24

[56] References Cited

U.S. PATENT DOCUMENTS

| | | | |
|---|---|---|---|
| 3,079 | 5/1845 | Rose | 482/13 |
| 2,890,697 | 6/1959 | Van Sickle | 128/200.23 |
| 3,900,138 | 8/1975 | Philips | 128/200.14 |
| 3,908,987 | 9/1975 | Boehringer | 482/13 |
| 4,452,239 | 6/1984 | Malem | 128/200.14 |
| 4,739,987 | 4/1988 | Nicholson . | |
| 5,007,419 | 4/1991 | Weinstein et al. | 128/200.14 |
| 5,018,517 | 5/1991 | Liardet . | |

FOREIGN PATENT DOCUMENTS

| | | | |
|---|---|---|---|
| 0804907 | 1/1969 | Canada | 482/13 |
| 0337990 | 5/1989 | European Pat. Off. . | |
| 0284810 | 11/1990 | Germany | 128/200.14 |
| 9202268 | 2/1992 | WIPO | 128/200.14 |
| 9204065 | 3/1992 | WIPO | 128/200.23 |
| 9303782 | 3/1993 | WIPO | 128/203.15 |

*Primary Examiner*—Richard J. Apley
*Assistant Examiner*—Jeanne M. Clark
*Attorney, Agent, or Firm*—Clifford W. Browning; Woodard, Emhardt, Naughton Moriarty & McNett

[57] ABSTRACT

The apparatus comprises a first tubular part (1) comprising an air inlet (4) wherein the patient may breathe out and in. A second part (2), inclined upwardly, comprises an outlet duct (5) having a conical shape and in which is disposed a spherical ball (6) having a diameter larger than the dimensions of the inlet orifice of the duct, in order to obstruct the duct before expiration. The axis of the conical duct (5) is inclined upwardly with respect to the axis of the tubular-shaped part (1). A third part (3) downwardly inclined comprises an outlet duct (5') having a conical shape and in which is disposed a spherical ball (6') having a diameter larger than the dimensions of the inlet orifice of the duct, in order to obstruct the duct before inspiration, the axis of said conical duct (5') being inclined with respect to the axis of the tubular-shaped part (1).

22 Claims, 7 Drawing Sheets

APPARATUS FOR RESPIRATORY THERAPY

The present invention relates to an apparatus for respiratory therapy.

An expiration-resisting apparatus designed for improving pulmonary ventilation is described in European Patent No. 0337990. This apparatus has small dimensions, is simple and not very expensive. It is easy to transport, for example in a pocket, and enables results to be obtained, which are equivalent to those obtained with appliances having a more complex design, which are generally very bulky and very expensive. It comprises a first part having a tubular shape and comprising an air inlet orifice into which the patient has to exhale and a second part comprising an outlet duct with a circular conical shape, in which is disposed a spherical ball having a diameter which is larger than the dimensions of the inlet orifice of the duct, so as to obstruct the duct before expiration. The axis of the conical duct is upwardly inclined with respect to the axis of the tubular-shaped part by an angle of between 30° and 80°. The angle formed by a generator of the wall of this duct and its axis is less than the angle of inclination of the axis of the duct. The apparatus also comprises one or more holes situated in a zone opposite the inlet orifice of the conical duct to enable the expired air to escape, the dimensions of the hole being chosen so as to prevent the ball escaping. Thus the ball may move freely in the duct by opposing a resistance to the expiration of the air expired by the patient, the lowest part of the duct forming a rolling bed for the ball, whereas the highest part of the duct forms a stop for the movement of the ball. Before expiration, the ball obstructs the duct of the cone. During expiration its instantaneous position results from a state of equilibrium between the pressure of expired air and the gravitational force of the ball combined with the slope of its race. Thus, during expiration, because of its very weak damping characteristic, the ball performs an oscillating movement which causes variable pressure which opposes expiration, by forming a positive oscillating resistance to expiration.

Experience has shown that this apparatus enables percussive ventilation of great efficiency, secretions being mobilised in a few minutes in the patient's bronchial tubes, enabling their easy expectoration. Measurements by oesophageal balloons have shown that the percussion phenomenon reaches the peripheral level of the lung. Clinical studies made have enabled an oscillating resistance to expiration COS (Controlled Oscillating System), which always has a positive value, adapted to known therapeutic values, to be revealed. These studies have also shown that the COS system enables the pressure to be automatically regulated and the frequency of the oscillation to be adapted, these two characteristics being inherent to the system and not dependent on the air throughput.

The synthesis of the clinical studies mentioned above, supplemented by very rigorous experimental observations, have enabled the curve of the opening/closing cycle of the apparatus described above to be drawn up.

Figure 11:
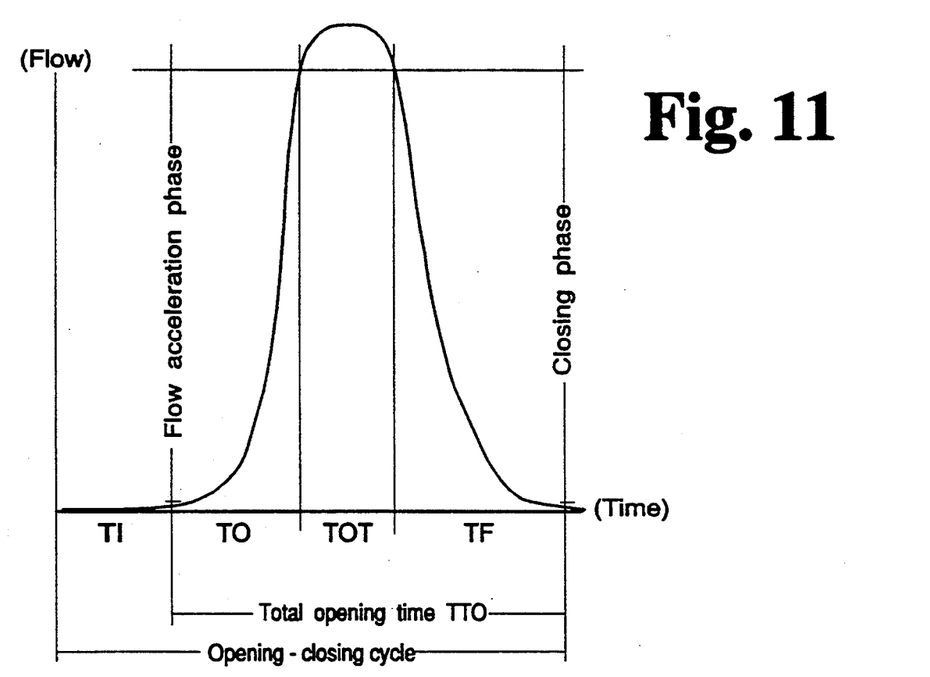
FIG. 11 is a diagram illustrating the principle of the opening/closing cycle of an expiration-resisting apparatus, such as that described in European Patent No. 0337990.
Figure 12:
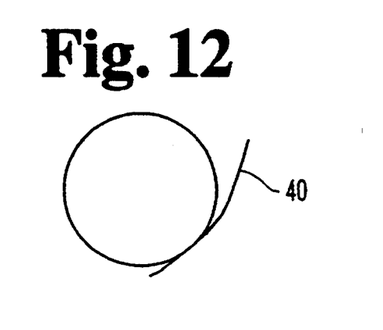
FIGS. 12 to 15 illustrate different forms of conical elements enabling the opening/closing cycle to be adapted to different specific therapeutic modes.
Figure 13:
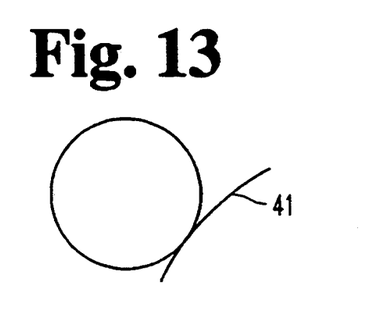
Figure 14:
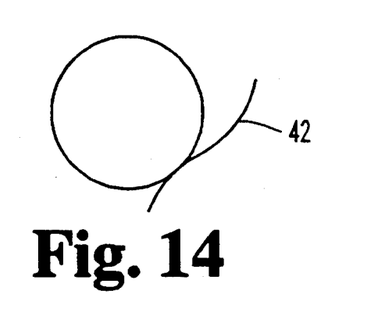
Figure 15:
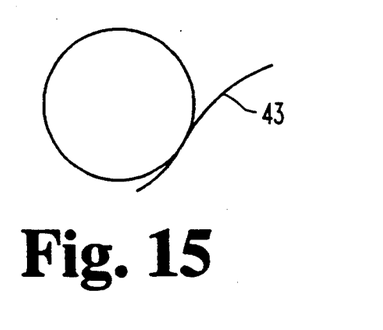

This curve, which is shown in FIG. 11, reveals the operating principle of the apparatus. After excess pressure, the ball which obstructs the duct moves and allows air to escape through an orifice, which increases as a function of its position (the speed of the mean expiratory flow is quasi not reduced). Then the pressure falls and the ball returns to its initial position in which it obstructs the orifice of the cone, again creating a determined excess pressure, which constitutes the beginning of a new cycle.

Therefore an opening/closing cycle comprises a total opening time TTO (=opening time TO+time of total opening TOT+closing time TF) and an interruption time TI.

It is during the interruption time TI that excess pressure is produced. The acceleration phase TO and the phase of total opening TOT enable a very great speed of the flow of air to be maintained, which, in addition to the therapeutic effect sought, greatly facilitates the use of the apparatus.

During the expiratory cycle, the ball therefore undergoes an oscillatory movement. The frequency of the oscillations, i.e. the number of opening/closing cycles per unit of time, may be modulated by the inclination of the apparatus by a few degrees above or below the horizontal.

It has also been noticed that when this expiration-resisting apparatus is used by a patient immediately after the inhalation of medication, the flow of turbulent air produced in the lungs during expiration into the apparatus firstly allows particles of medication to penetrate further into the bronchial tubes and secondly an improvement in the deposit of these particles in the lungs.

The object of the present invention is to make profitable use of the above observations and to propose a specific apparatus for the respiratory field which is designed according to the basic principle of the apparatus described above, but offering improved and/or greater therapeutic possibilities.

For this purpose, the present invention relates to an apparatus for respiratory therapy, as defined in claim 1.

Such an apparatus enables a therapeutic effect to be obtained both during expiration and also during inspiration.

According to an embodiment, the apparatus enables percussive ventilation having the effects described above to be obtained, both during expiration and during inspiration.

According to another embodiment the apparatus is designed to enable not only percussive pulmonary ventilation, but also to favour the taking of medications.

The invention also relates to an element having a conical duct for the apparatus for respiratory therapy according to the precharacterising clause of claim 22, as defined in the characterising part of claim 22, and also an apparatus for respiratory therapy comprising such an element having a conical duct, as specified in claim 27.

According to an embodiment, the apparatus is designed to obtain a therapeutic effect during expiration and/or inspiration and is provided with a set of interchangeable conical elements, the shape of each of the conical elements being designed so as to permit an adaptation of the opening/closing cycle to different specific therapeutic modes.

This interchangeability enables the therapist to adapt very precisely the operation of the apparatus to the precise characteristics of the therapy which he wishes to be adopted by the patient, by altering the relationship between the interruption time TI (excess pressure phase), the opening time TO (flow acceleration phase), time of total opening TOT (free outlet) and closing time TF.

The following description, given by way of example, refers to the attached drawings on which.

Figure 1:
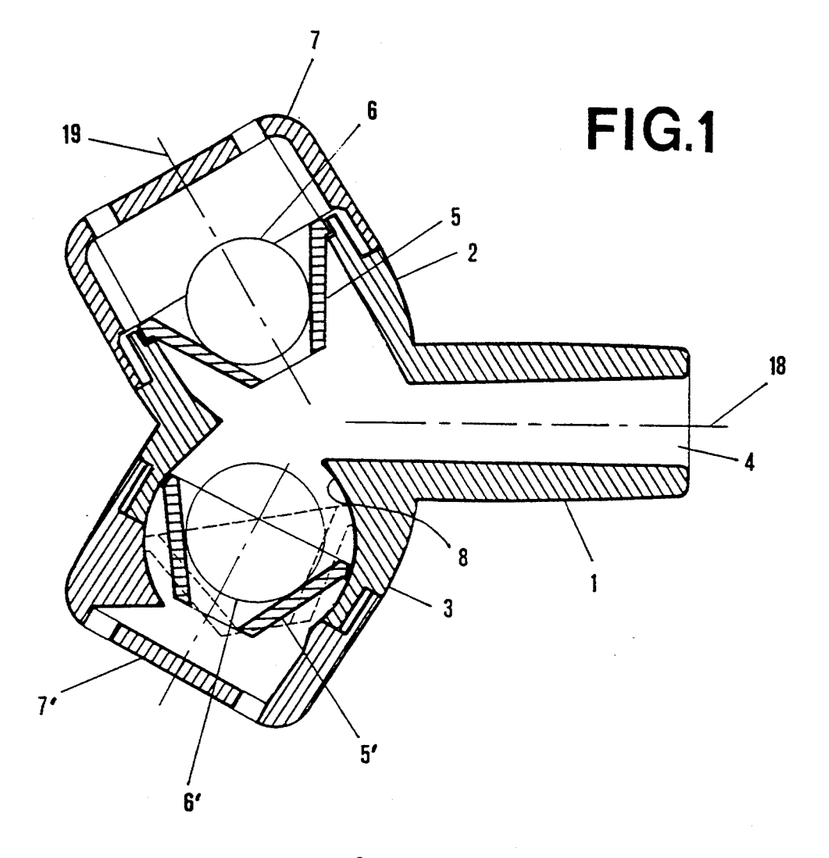
FIG. 1 is a diagrammatical vertical section of an exemplified embodiment of a double-action apparatus according to the invention, both during expiration and during inspiration.

The apparatus shown in FIG. 1 is a double-action apparatus which enables percussive pulmonary ventilation to be obtained both during expiration and also during inspiration. It comprises an element in the shape of a double pipe, comprising a first rectilinear tubular part 1, a second part 2 upwardly inclined with respect to the first part and a third part 3 downwardly inclined with respect to the first part. The first tubular part comprises an air inlet orifice 4 into which the patient may either exhale or inhale. Each of the second and third parts comprises an element 5, respectively 5', in the form of a truncated cone, and a ball 6, respectively 6', the diameter of which is greater than the smallest diameter of the corresponding conical element. The cone 5 of the upwardly inclined part is disposed so that its orifice having the larger diameter is situated pointing upwards, and that the ball rests inside the cone of the walls of said cone, the characteristics of this part of the apparatus being those of the apparatus described in European Patent No. 0337990, which was mentioned above. Similarly the cone 5' disposed in the downwardly inclined part is turned so that its orifice having the larger diameter is also situated at the top, i.e. in this case towards the interior of the apparatus, so that, in the inoperative position, the second ball comes to rest on the internal walls of the cone and obstructs the duct. The apparatus also comprises two covers 7, 7' disposed respectively at the end of each of the upwardly inclined and downwardly inclined parts 2, 3, said covers having holes so as to enable firstly exhaled air to escape though the first cover 7 and secondly inhaled air to be admitted through the second cover 7'. A result of the arrangement described above is that, during an expiration, the orifice formed by the downwardly inclined part is closed by the obstruction of the second ball 6' in the lower cone 5' under the action of the air pressure, whereas the air escapes through the upwardly inclined part, the first ball 6 moving under the action of the expiration and producing the percussive ventilation effect already described above. During an inspiration the orifice formed by the upwardly inclined part is obstructed by the first ball 6 under the action of its own weight, whereas the ball 6' disposed in the lower cone rises so as to enable the passage of air, as a result of which there is percussive ventilation of the same type as that which occurs during expiration. The covers 7, 7' and also the cones 5, 5' can be removed, so as to enable in particular the apparatus to be efficiently cleaned.

The cone 5' of the downwardly inclined part may be inclined in the same direction as the upper cone, so that its axis is roughly parallel to that of the upper cone, as shown by broken lines in FIG. 1. It may also be inclined in the opposite direction to the upper cone, as shown by unbroken lines in FIG. 1. The angles of inclination of the cones will be chosen so as to prevent the balls becoming raised and floating above their support, but so that they remain in contact therewith, so as to obtain the best desired percussive effect. According to the embodiment shown in FIG. 1, the lower cone is pivoted inside a spherical element 8, which enables the inclination of the cone to be varied by acting, for example, on an operating member, such as an axle (not shown) protruding from the exterior of the apparatus.

Upwardly inclined part 2 and downwardly inclined part 3 of the double-action apparatus shown in FIG. 1 roughly have the same dimensions. However it will be noted that such a similarity in dimensions is in no way necessary and that the downwardly inclined part may be made with dimensions which are smaller (or respectively greater) than those of the upwardly inclined part and therefore with a cone and a ball of dimensions which are smaller (or respectively greater) than those of the cone and of the ball of the upper part, according to the function(s) assigned to the apparatus and/or the therapeutic effect sought.

Figure 2:
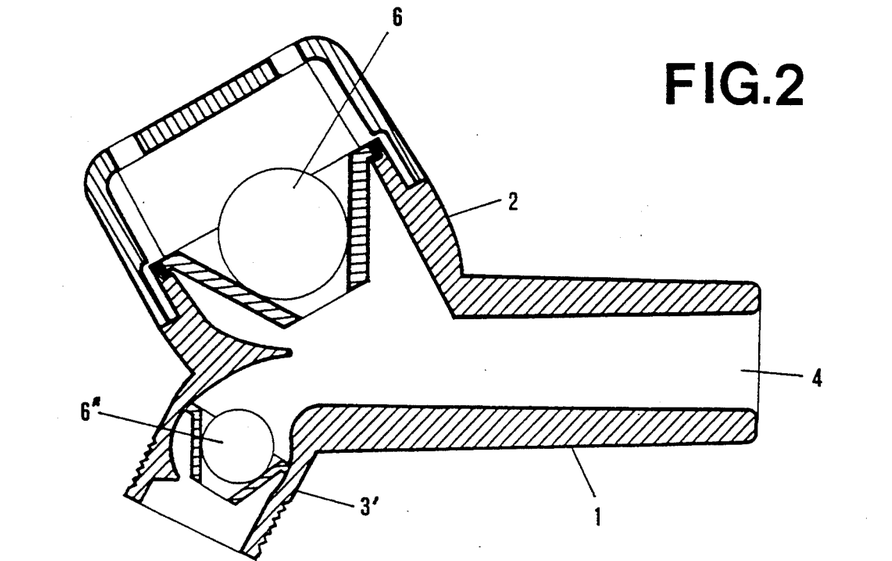
FIG. 2 is a diagrammatical vertical section of an exemplified embodiment of the apparatus according to the invention provided with an inspiration valve, especially for taking medication.

On the other hand it is possible to design the appliance, as shown on FIG. 2, with a light lower ball 6", in which case the apparatus does not produce the percussive effect of the apparatus in FIG. 1 during an inspiration, but only a valve effect which enables, in particular, a medication to be taken. The lower ball 6" of the apparatus shown in FIG. 2 has smaller dimensions than those of the upper ball 6. Of course it is also possible to produce the same type of apparatus with a light lower ball, but having greater dimensions than those of the upper ball. In the two cases, the support cone for the lower ball 6" will be preferably disposed so that its axis is inclined, so that the ball does not rise, but remains in contact with the cone. In fact, if the axis of the cone is vertical, the ball rises and tends to perform movements describing convolutions along the walls of the cone, which slows down the closing movement. In contrast, when the axis of the cone is inclined so that the ball remains in contact with the cone and the cone forms a ball race, the closing movement is faster.

Figure 3:
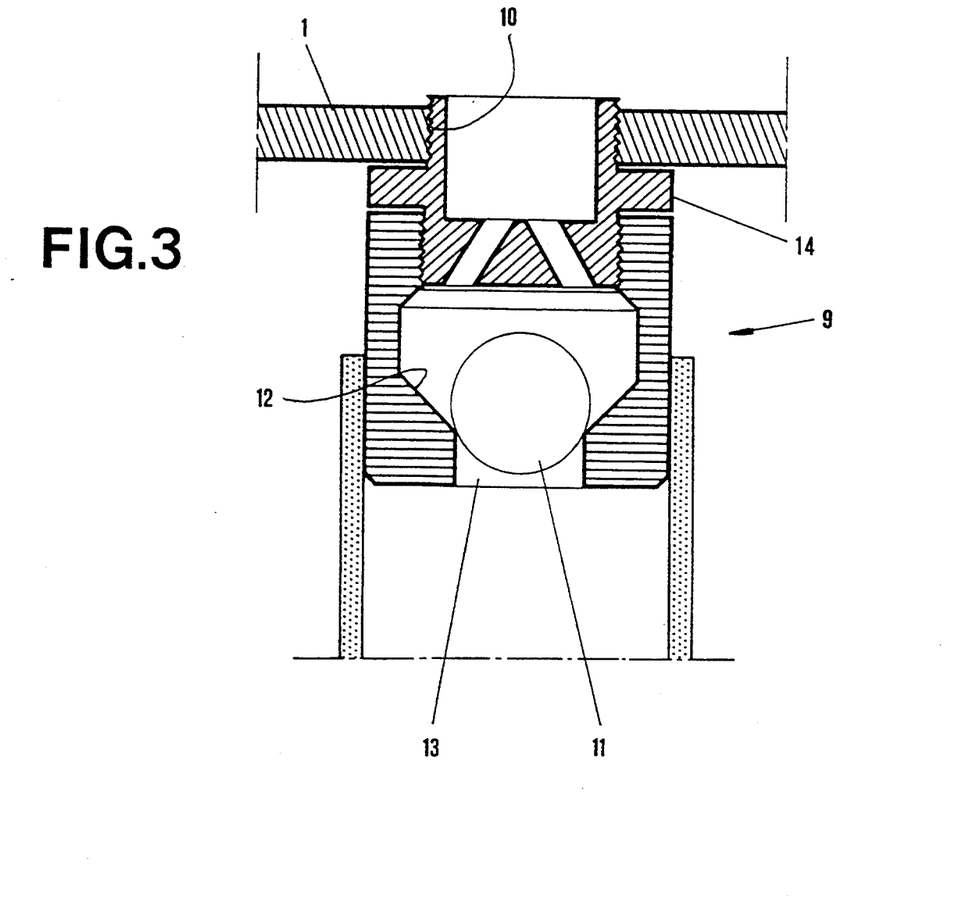
FIG. 3 is a vertical section of a detail of a refinement of the inspiration valve.

According to a refinement of the apparatus in FIG. 2, the downwardly inclined part 3' may be replaced by a simple orifice 10 made in the lower part of the first rectilinear tubular part 1, close to the bent part. A device 9 which enables a medication to be taken during an inspiration is mounted on the apparatus at the site of this orifice, for example by a threaded joint. As shown in FIG. 3, this device comprises an inspiration valve, fixed to the apparatus by means of a vent adapter 14. The valve is designed to be closed in the inoperative state or during an expiration, but to open during an inspiration. The valve comprises a ball 11 which in the inoperative state remains on the conical edge 12 of an aperture 13 of the device for dispensing medication. Of course, any other adequate form of valve could be provided.

Figure 4:
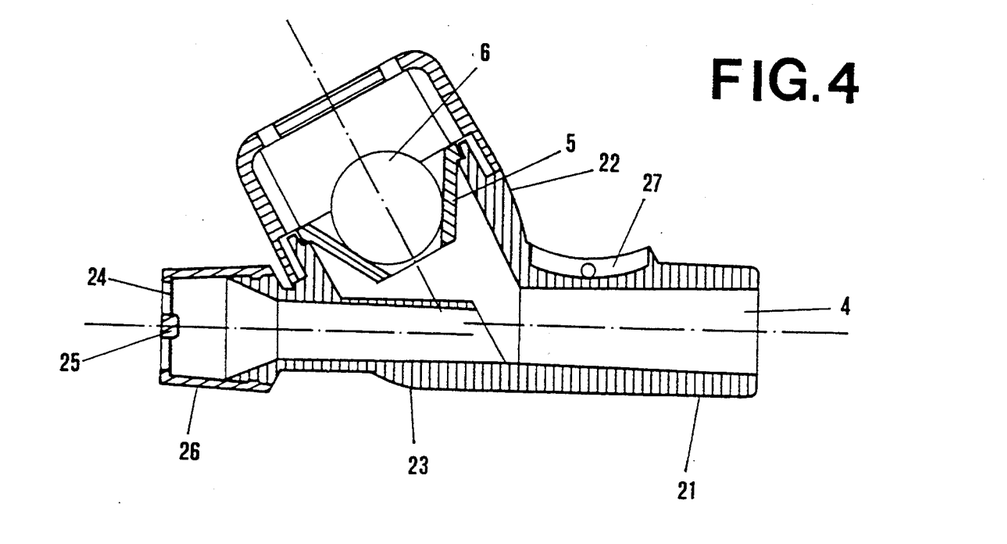
FIG. 4 is a diagrammatical vertical section of an exemplified embodiment of the apparatus according to the invention which can be connected both to an aerosol and also to a spray metering device.
Figure 5:
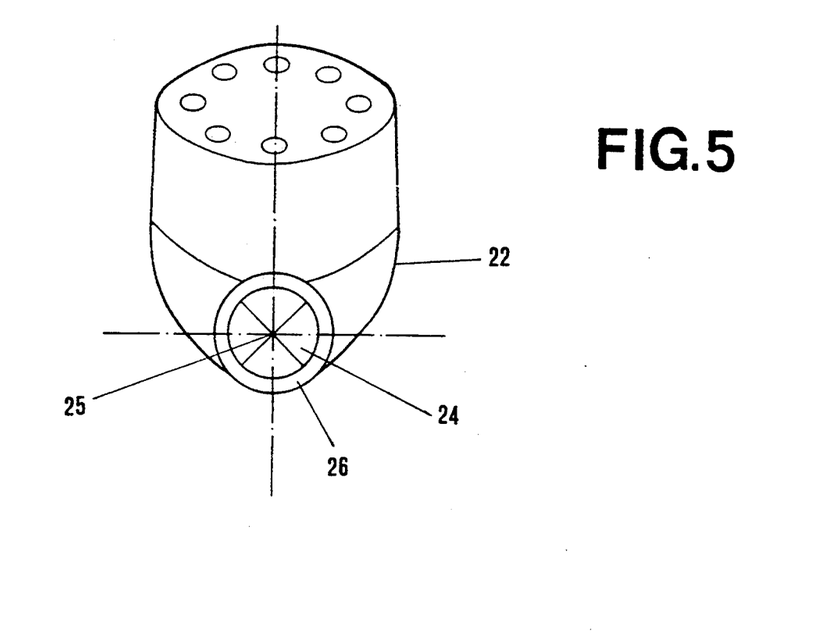
FIG. 5 is a view from the front of the apparatus of FIG. 4.
Figure 6:
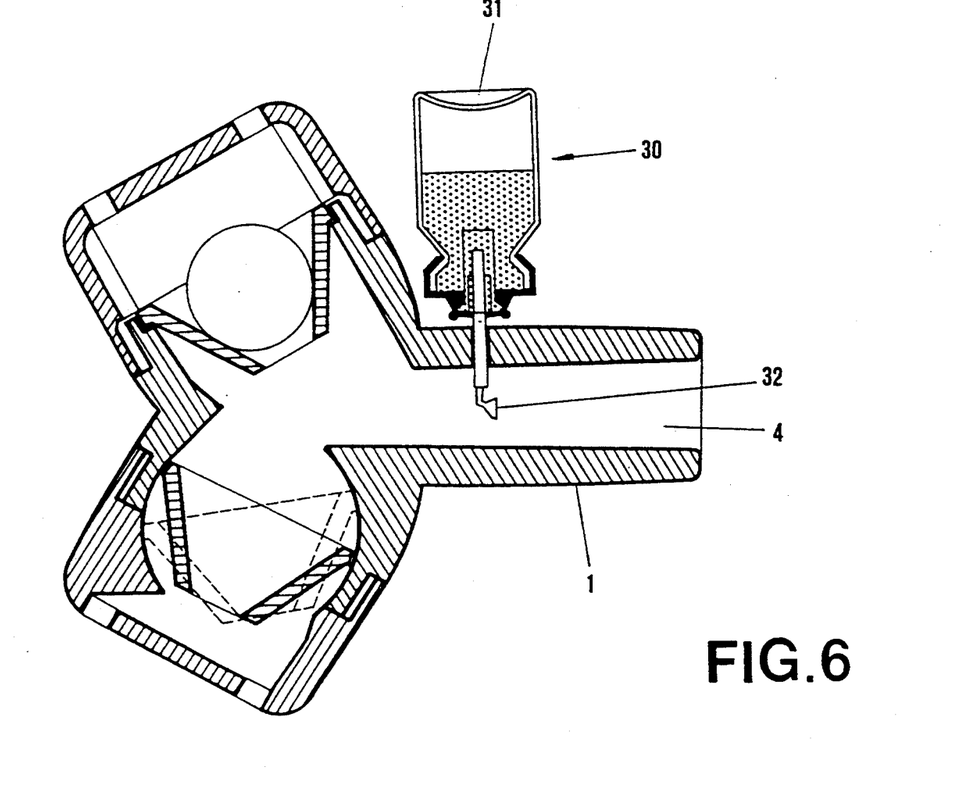
FIG. 6 is a diagrammatical vertical section of another example of a double-action apparatus, combined with an aerosol metering device.
Figure 7:
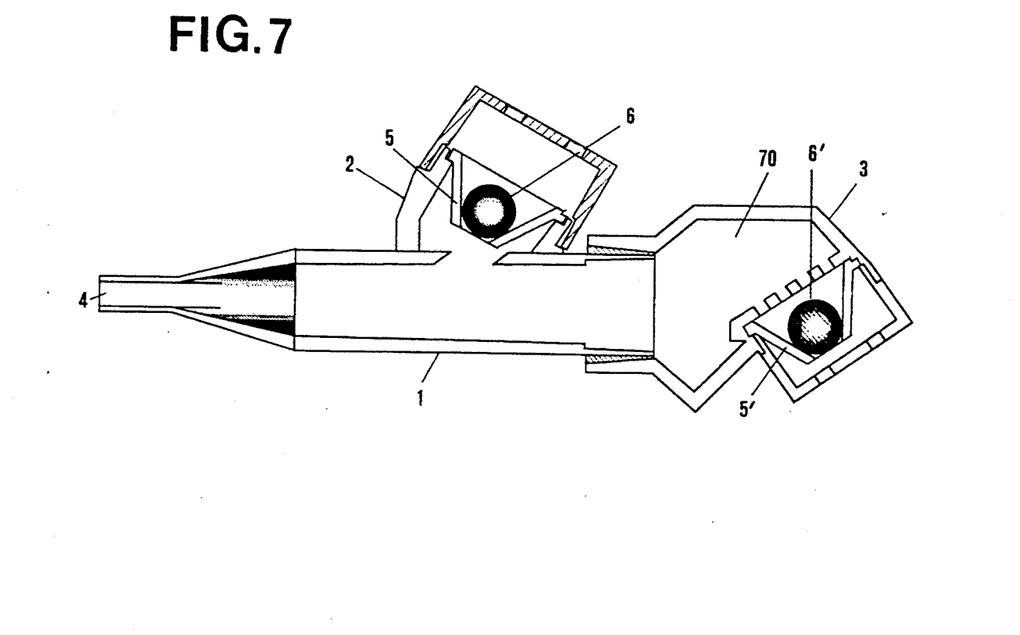
FIG. 7 is a diagrammatical vertical section of another example of a double-action apparatus.
Figure 8:
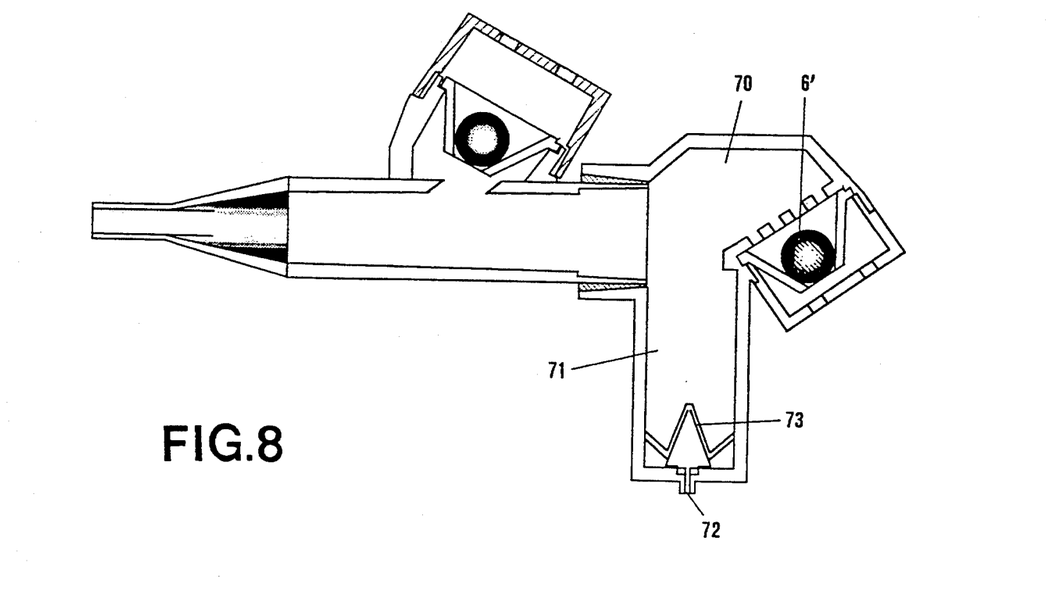
FIG. 8 is a diagrammatical vertical section of an example of an apparatus comprising a nebulisation chamber.
Figure 9:
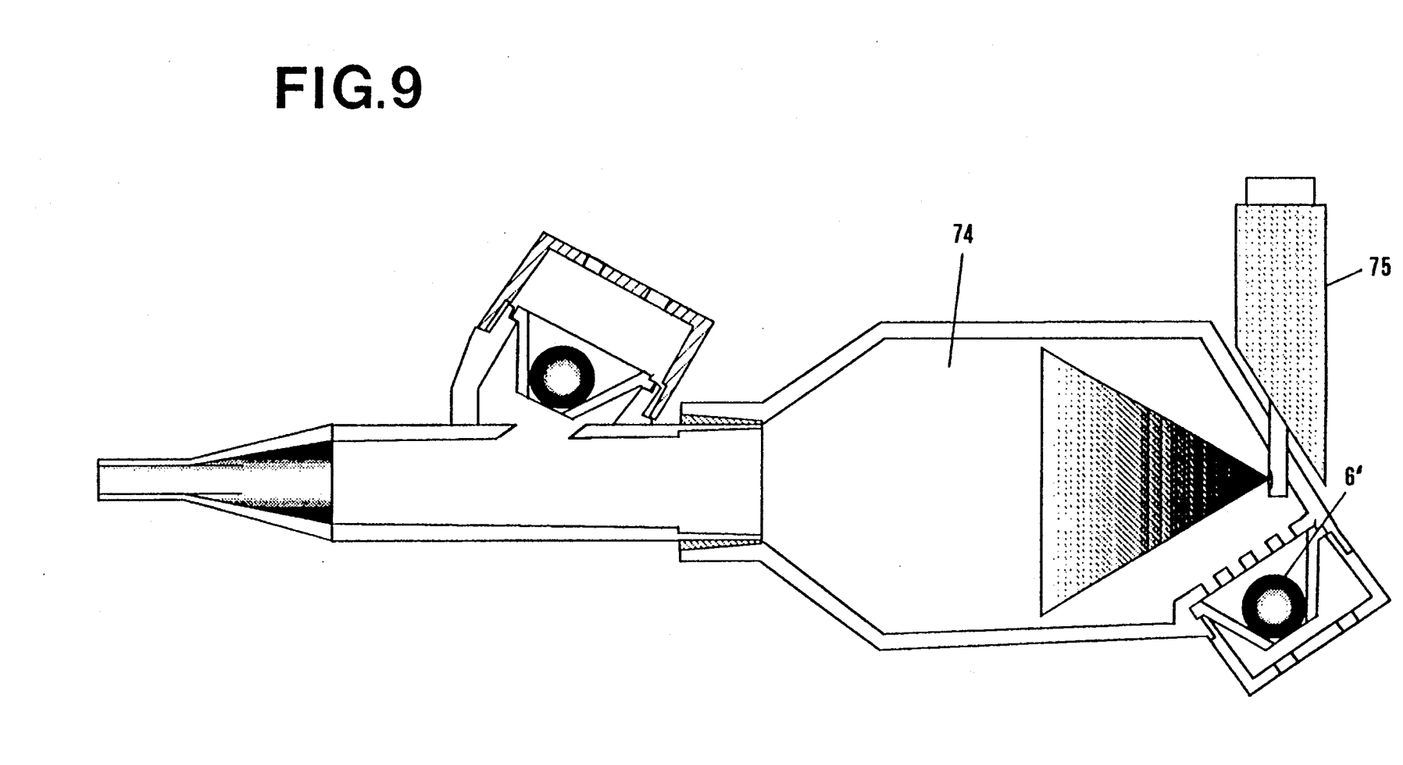
FIG. 9 is a diagrammatical vertical section of another example of an apparatus equipped with a spray metering device.
Figure 10:
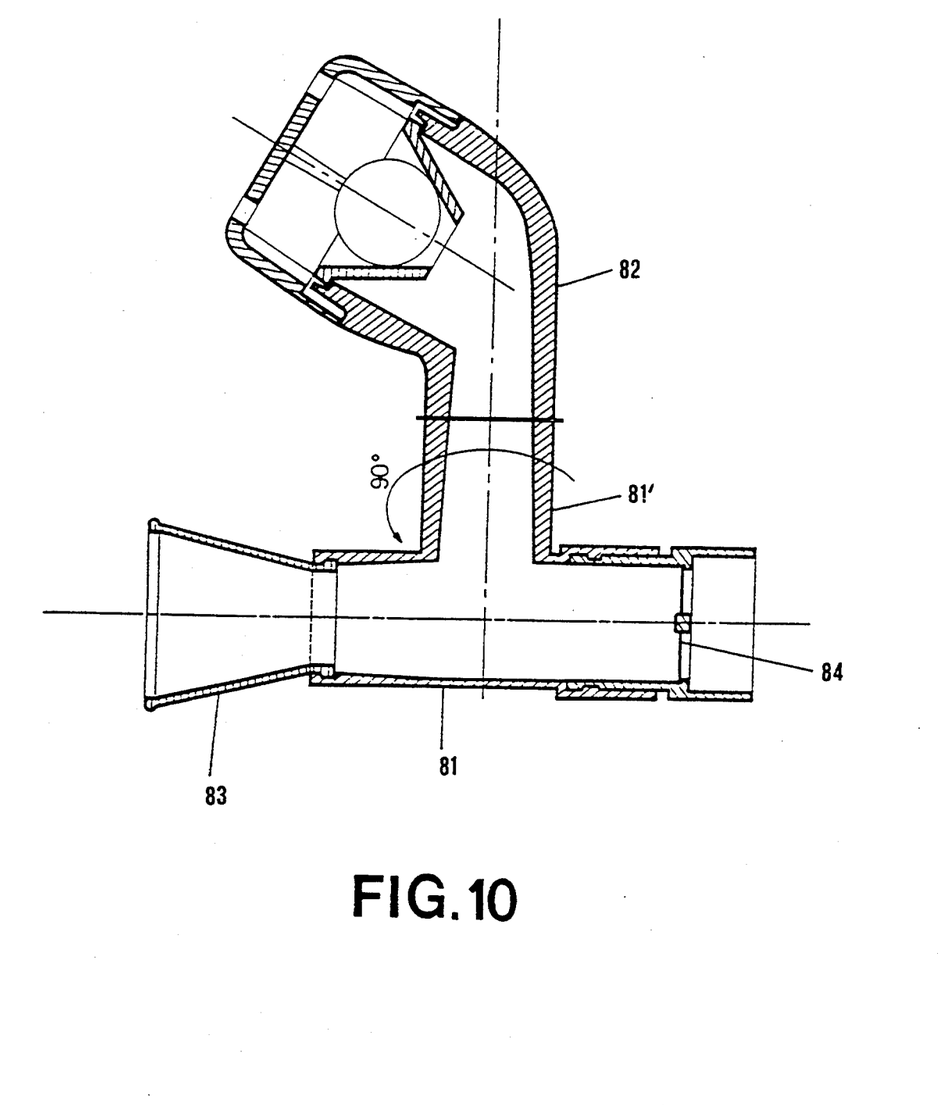
FIG. 10 is a diagrammatical vertical section of a refinement of the apparatus in FIG. 4.

The apparatus diagrammatically shown in FIGS. 4 and 5 comprises the traditional elements already described which allow percussive pulmonary ventilation during the expiration of the patient. The rectilinear tubular part 21 which forms the mouthpiece of the apparatus is extended at its other end, after the upwardly inclined part 22, by a portion of rectilinear tubular element 23, the axis of which is parallel to that of the mouthpiece. This portion may comprise a valve 24 at its end, for example in the form of a flexible rubber disk which is fixed at its centre 25 to the end of an element in the form of a slightly conical tube 26. The element 26 is mounted, for example by clipping, to the front end of the portion of tubular element 23. The conical shape of the element 26 enables a hose connected to an aerosol compressor or to a spray metering device to be fixed there, by simply introducing the end of the hose around part 26 and forcing it. The same assembly may be provided on the valve element in FIGS. 2 and 3. The apparatus may comprise a level 27 enabling its inclination to be controlled. Furthermore, a chamber of the "spacer" type may be inserted between the apparatus and the hose so as to create a reserve of product to be inhaled.

FIG. 6 illustrates a double-action apparatus combined with an aerosol metering device 30 mounted on the upper part of the mouthpiece end 1, the aerosol metering device being designed so that pressure on its base 31 injects a dose 32 of medication inside the mouthpiece 4.

The apparatus shown in FIG. 7 is a double-action apparatus which enables the same effects to be obtained as the apparatus shown in FIG. 1. As in FIG. 1, there are a first rectilinear tubular part 1, a second upwardly inclined part 2 and a third downwardly inclined part 3. However the third part is offset towards the front with respect to the second part and mounted in a movable manner, for example by a simple conical fitting at the end of the first part, so as to form a modular apparatus. This modular design facilitates firstly the dismantling of the apparatus so that it can be cleaned and secondly enables the apparatus to be easily modified in order to obtain, for example, one of the configurations shown in FIGS. 8 and 9.

Thus, according to the configuration of the apparatus shown in FIG. 8, the third part comprises an enlarged space 70 when compared with the space in FIG. 7, so as to form, for example, a nebulisation chamber 71, equipped with an orifice 72 which enables its connection to a compressor. As shown in FIG. 8, the nebuliser 73 may be housed inside the chamber 71.

Similarly, according to the configuration shown in FIG. 9, the third part of the apparatus comprises a chamber 74, on which is mounted a spray metering device 75, said chamber forming what is called in technical language a "spacer", which is intended to put at the patient's disposal a greater, more homogenous volume of particles and to create a reserve of product to be inhaled, enabling a better intake of particles by the patient.

Of course, ball 6' in any one of the apparatuses shown on FIGS. 7 and 9 may be a light ball, which therefore no longer has any function but that of a valve.

It will also be noted that it is possible to replace the mouthpiece of each of the apparatuss described above by a connecting device which enables the apparatus to be integrated in a respiratory support system.

The apparatus shown in FIG. 10 is a refinement of the apparatus shown in FIG. 4. It comprises a T-shaped tubular element 81 equipped with an expiration resistance element 82, and comprising a mouthpiece 83 at one of its lateral ends and a valve 84 at its opposite end. For reasons relating to the representation, element 82 has been shown in the same plane as the T-shaped tubular element. In reality, tubular element 81 is perpendicular to the drawing plane.

In order to enable the therapist to refine his treatment as a function of the parameters of the patient to be treated, conical element 5, in the case of a single-action apparatus for expiration, and/or conical element 5', in the case of a double-action apparatus, may be designed so that the generator of the cone has a form (as shown for example in one of FIGS. 12 to 15) determined as a function of a particular opening cycle of the duct. Similarly, in order to develop the treatment for a given patient, each of the apparatuses described above may be produced with an air outlet duct, and/or if need be, with an air intake duct, comprising a removable conical element, with a set of interchangeable conical elements being provided, each of said conical elements having a shape designed to correspond to a particular opening/-closing cycle of the duct (FIG. 11).

Different shapes of cones may be specified depending on the desired effect. The various shapes worthy of consideration may be regrouped into four groups, which are represented in FIGS. 12 to 15.

The first group relates to conical elements 40 having a generator having a concave shape (FIG. 12). Such a shape enables the excess pressure phase (interruption time TI) to be reduced, the opening time to be increased, as well as the frequency of the oscillations and possibly the time of total opening, and the acceleration of the flow to be reduced.

The second group concerns conical elements 41 having a generator having a convex shape (FIG. 13). Such a shape enables the excess pressure phase to be increased (increase in the time TI), the opening time to be reduced, as well as the frequency of the oscillations, whilst increasing the time of total opening and the acceleration of the flow.

The third group relates to conical elements 42, the generater of which comprises a lower part having a convex shape and an upper part with a concave shape (FIG. 14).

The fourth group comprises conical elements 43, the generator of which comprises a lower part having a concave shape and an upper part having a convex shape (FIG. 15).

Other shapes or combinations of shapes may of course be possible.

I claim:

1. An apparatus for respiratory therapy comprising a first part (1) having a tubular shape with a first axis (18) and having a first air inlet orifice (4) into which the patient may exhale and a second part (2) in fluid communication with the first part (1) having means for producing a variable pulmonary ventilation when the patient expires, said means for producing including an air expiration duct (5) having a conical shape with a second axis (19) and a second air inlet orifice and an air outlet orifice, in which is disposed a first spherical ball (6) having a diameter larger than the dimensions of the second air inlet orifice of the air expiration duct, in order to obstruct the air expiration duct before expiration by the patient, the second axis (19) of the air expiration duct being upwardly inclined with respect to the first axis (18) of the tubular-shaped first part (1), the angle formed by the wall of the air expiration duct (5) and its second axis (19) being less than the angle of inclination of the second axis (19) with respect to the first axis (18) of the tubular-shaped first part (1), the apparatus being designed so as to enable expired air to escape through at least one hole in said second part beyond the air outlet orifice of said air expiration duct; and the apparatus further comprising at least a third air orifice including an opening means designed to open during an inspiration of the patient, wherein the means designed to open during inspiration includes an air inspiration duct (5') having a conical shape with a third axis and a fourth air inlet orifice and a second air outlet orifice, in which is disposed a second spherical ball (6') having a diameter which is greater than the dimensions of the fourth air inlet orifice of the inspiration duct, so as to obstruct the inspiration duct before inspiration by the patient.

2. An apparatus according to claim 1, wherein the third axis of the inspiration duct is inclined with respect to the first axis (18) of the tubular-shaped part, the angle formed by the wall of this duct and its third axis being less than the angle of inclination of the third axis with respect to the first axis of the tubular-shaped part.

3. An apparatus according to claim 2, and further comprising means (3, 5', 6') for producing a variable pulmonary ventilation during the inspiration of the patient to enable percussive ventilation during expiration.

4. An apparatus according to claim 3, arranged so that the means designed to open during expiration and inspiration are separated by an internal space or volume (70, 71, 74).

5. An apparatus according to claim 4, wherein said internal space constitutes a mixing space of the "spacer" type.

6. An apparatus according to claim 1, and further comprising an inspiration valve intended for the taking of a medication.

7. An apparatus according to claim 6, wherein the inspiration valve includes means for its connection to a spray metering device.

8. An apparatus according to claim 7, arranged so that the means designed to open during expiration and inspiration are separated by an internal space or volume (70, 71, 74).

9. An apparatus according to claim 1, and further comprising a spray metering device mounted on the apparatus, including means designed for the injection of a medication into the apparatus.

10. An apparatus according to claim 9, arranged so that the means designed to open during expiration and inspiration are separated by an internal space or volume (70, 71, 74).

11. A conical duct element for a specific therapeutic apparatus in the respiratory field comprising a first tubular-shaped part (1) with a first axis (18) having a first air inlet orifice (4) into which the patient may exhale and a second part in fluid communication with the first part having means for producing a variable pulmonary ventilation during the expiration of the patient, said means for producing including an air expiration duct (5) having a conical shape with a second axis (19) and a second air inlet orifice and an air outlet orifice, in which is disposed a first spherical ball (6) having a diameter larger than the dimensions of the inlet orifice to the air expiration duct, so as to obstruct the air expiration duct before expiration by the patient, the second axis (19) of the air expiration duct being upwardly inclined with respect to the first axis (18) of the tubular-shaped part, the angle formed by the wall of the air expiration duct and its second axis being less than the angle of inclination of the second axis with respect to the first axis of the tubular-shaped part, the apparatus being designed so as to enable the expired air to escape from said second part through at least one hole in said second part beyond the air outlet orifice of said air expiration duct, wherein the wall of the conical air expiration duct has a concave shape.

12. A conical duct element for a specific therapeutic apparatus in the respiratory field comprising a first tubular-shaped part (1) with a first axis (18) having a first air inlet orifice (4) into which the patient may exhale and a second part in fluid communication with the first part having means for producing a variable pulmonary ventilation during the expiration of the patient, said means for producing including an air expiration duct (5) having a conical shape with a second axis (19) and a second air inlet orifice and an air outlet orifice, in which is disposed a first spherical ball (6) having a diameter larger than the dimensions of the inlet orifice to the air expiration duct, so as to obstruct the air expiration duct before expiration by the patient, the second axis (19) of the air expiration duct being upwardly inclined with respect to the first axis (18) of the tubular-shaped part, the angle formed by the wall of the air expiration duct and its second axis being less than the angle of inclination of the second axis with respect to the first axis of the tubular-shaped part, the apparatus being designed so as to enable the expired air to escape from said second part through at least one hole in said second part beyond the air outlet orifice of said air expiration duct, wherein the wall of the conical air expiration duct has a convex shape.

13. A conical duct element for a specific therapeutic apparatus in the respiratory field comprising a first tubular-shaped part (1) with a first axis (18) having a first air inlet orifice (4) into which the patient may exhale and a second part in fluid communication with the first part having means for producing a variable pulmonary ventilation during the expiration of the patient, said means for producing including an air expiration duct (5) having a conical shape with a second axis (19) and a second air inlet orifice and an air outlet orifice, in which is disposed a first spherical ball (6) having a diameter larger than the dimensions of the inlet orifice to the air expiration duct, so as to obstruct the air expiration duct before expiration by the patient, the second axis (19) of the air expiration duct being upwardly inclined with respect to the first axis (18) of the tubular-shaped part, the angle formed by the wall of the air expiration duct and its second axis being less than the angle of inclination of the second axis with respect to the first axis of the tubular-shaped part, the apparatus being designed so as to enable the expired air to escape from said second part through at least one hole in said second part beyond the air outlet orifice of said air expiration duct, wherein the wall of the conical air expiration duct comprises a convex-shaped lower part and a concave-shaped upper part.

14. A conical duct element for a specific therapeutic apparatus in the respiratory field comprising a first tubular-shaped part (1) with a first axis (18) having a first air inlet orifice (4) into which the patient may exhale and a second part in fluid communication with the first part having means for producing a variable pulmonary ventilation during the expiration of the patient, said means for producing including an air expiration duct (5) having a conical shape with a second axis (19) and a second air inlet orifice and an air outlet orifice, in which is disposed a first spherical ball (6) having a diameter larger than the dimensions of the inlet orifice to the air expiration duct, so as to obstruct the air expiration duct before expiration duct by the patient, the second axis (19) of the air expiration duct being upwardly inclined with respect to the first axis (18) of the tubular-shaped part, the angle formed by the wall of the air expiration duct and its second axis being less than the angle of inclination of the second axis with respect to the first axis of the tubular-shaped part, the apparatus being designed so as to enable the expired air to escape from said second part through at least one hole in said second part beyond the air outlet orifice of said air expiration duct, wherein the wall of the conical air expiration duct comprises a concave-shaped lower part and a convex-shaped upper part.

15. A conical duct element for a specific therapeutic apparatus in the respiratory field comprising a first tubular-shaped part (1) with a first axis (18) having a first air inlet orifice (4) into which the patient may exhale and a second part in fluid communication with the first part having means for producing a variable pulmonary ventilation during the expiration of the patient, said means for producing including an air expiration duct (5) having a conical shape with a second axis (19) and a second air inlet orifice and an air outlet orifice, in which is disposed a first spherical ball (6) having a diameter larger than the dimensions of the inlet orifice to the air expiration duct, so as to obstruct the air expiration duct before expiration by the patient, the second axis (19) of the air expiration duct being upwardly inclined with respect to the first axis (18) of the tubular-shaped part, the angle formed by the wall of the air expiration duct and its second axis being less than the angle of inclination of the second axis with respect to the first axis of the tubular-shaped part, the apparatus being designed so as to enable the expired air to escape from said second part through at least one hole in said second part beyond the air outlet orifice of said air expiration duct, wherein the air expiration duct is made in the form of at least one removable element in the shape of a truncated cone having a shape designed in order to obtain a determined opening/closing cycle of the apparatus during the displacement of the first spherical ball during expiration of the patient.

16. An apparatus according to claim 15, and further comprising at least a third air orifice including an opening means designed to open during an inspiration of the patient.

17. An apparatus according to claim 16, wherein the angle formed by the second axis of the expiration duct and the first axis of the tubular-shaped part is between 30° and 80°.

18. An apparatus according to claim 17, wherein the means designed to open during inspiration includes an air inspiration duct (5') having a conical shape with a third axis and a fourth air inlet orifice and a second air outlet orifice, in which is disposed a second spherical ball (6') having a diameter which is greater than the dimensions of the fourth air inlet orifice of the air inspiration duct, so as to obstruct the air inspiration duct before inspiration by the patient.

19. An apparatus according to claim 18, wherein the third axis of the inspiration duct is inclined with respect to the first axis (18) of the tubular-shaped part, the angle formed by the wall of this duct and its third axis being less than the angle of inclination of the third axis with respect to the first axis of the tubular-shaped part.

20. An apparatus according to claim 19, and further comprising a spray metering device mounted on the apparatus including means designed for the injection of a medication into the apparatus.

21. An apparatus according to claim 20, wherein the means designed to open during expiration and inspiration are separated by an internal space or volume (70, 71, 74).

22. An apparatus for respiratory therapy comprising a first part (1) having a tubular shape with a first axis (18) and having a first air inlet orifice (4) into which the patient may exhale and a second part (2) in fluid communication with the first part having means for producing a variable pulmonary ventilation, namely a percussion effect, when the patient expires, said means for producing including an air expiration duct (5) having a conical shape with a second axis (19) and a second air inlet orifice and an air outlet orifice, in which is disposed a first spherical ball (6) having a diameter larger than the dimensions of the second air inlet orifice of the air expiration duct, in order to obstruct the air expiration duct before expiration by the patient, the second axis (19) of the air expiration duct being upwardly inclined with respect to the first axis (18) of the tubular-shaped first part, the angle formed by the wall of the air expiration duct (5) and its second axis (19) being less than the angle of inclination of the second axis (19) with respect to the first axis (18) of the tubular-shaped first part, the apparatus being designed so as to enable expired air to escape through at least one hole in said second part beyond the air outlet orifice of said air expiration duct from said second part; the apparatus further comprising at least a third air orifice including an opening/closing means designed to open during an inspiration of the patient, said opening/closing means being arranged for the taking of a medication, whereby the apparatus allows improvement in the taking of medications by associating the taking with an effect resulting from the pulmonary ventilation, namely the percussion effect.

* * * * *